United States Patent [19]
Lal et al.

[11] Patent Number: 5,520,661
[45] Date of Patent: May 28, 1996

[54] FLUID FLOW REGULATOR

[75] Inventors: Birendra K. Lal, Lake Zurich; Yuan-Pang S. Ding, Vernon Hills; Michael R. Prisco, Aurora; Rebecca S. Black; Robert Passaglia, both of Arlington Heights; James Richardson, Schaumburg, all of Ill.

[73] Assignee: Baxter International Inc., Deerfield, Ill.

[21] Appl. No.: 279,938

[22] Filed: Jul. 25, 1994

[51] Int. Cl.$^6$ ................................................. A61M 5/00
[52] U.S. Cl. ........................... 604/246; 604/30; 604/256; 137/843
[58] Field of Search ................... 137/843, 846, 137/847, 848, 849, 850, 852, 854, 855; 604/9, 30, 80, 81, 86, 905, 91, 246, 247, 245, 256, 323, 257, 262, 408, 410, 415, 185, 326, 167

[56] References Cited

U.S. PATENT DOCUMENTS

| | | |
|---|---|---|
| 4,142,523 | 3/1979 | Stegeman . |
| 4,222,407 | 9/1980 | Ruschke et al. ................ 137/843 |
| 4,286,628 | 9/1981 | Paradis et al. ................. 137/843 |
| 4,343,305 | 8/1982 | Bron . |
| 4,369,812 | 1/1983 | Paradis et al. ................. 137/843 |
| 4,415,003 | 11/1983 | Paradis et al. ................. 137/843 |
| 4,515,588 | 5/1985 | Amendolia . |
| 4,769,012 | 9/1988 | Quang et al. . |
| 4,925,451 | 5/1990 | Amendolia . |
| 4,966,199 | 10/1990 | Ruschke ........................ 137/843 |

OTHER PUBLICATIONS

"Product Specification of the ISOFLUX (R) Flow Regulator," 8 pages Van Leer Medical, France Known to Applicants at least just prior to filing the application.

Primary Examiner—Corrine M. Maglione
Assistant Examiner—N. Kent Gring
Attorney, Agent, or Firm—Jeffrey C. Nichols; Paul C. Flattery

[57] ABSTRACT

The present invention provides an intravenous fluid flow regulator 10 for controlling the I.V. administration of medical fluid to a patient. The fluid flow regulator 10 provides a housing 12 having a top 18 and a bottom 20. A flexible diaphragm 14 is positioned within housing 12. A diaphragm holder 16 is provided inside housing 12 for holding a sealing edge 56 of flexible diaphragm 14 in fluid sealing engagement with diaphragm holder 16. The housing 12 and flexible diaphragm 14 define an inlet fluid reservoir 62 and an outlet fluid reservoir 64. The diaphragm holder 16 defines a by-pass fluid channel 54 from inlet fluid reservoir 62, around diaphragm 14, to outlet fluid reservoir 64. The flexible diaphragm 14 being flexible to alternatively move into inlet fluid reservoir 62 and outlet fluid reservoir 64 depending on a fluid pressure differential between inlet fluid reservoir 62 and outlet fluid reservoir 64. A fluid inlet 24 is connected to housing top 18 to provide an inlet fluid passage 27 from an I.V. bag containing medical fluid to inlet fluid reservoir 62. A fluid outlet 34 is connected to housing bottom 20 to provide an outlet fluid passage 44 from outlet fluid reservoir 64 to the patient. At least one rib 48 connected to bottom 20 is provided to prevent movement of flexible diaphragm 14 into outlet fluid reservoir 64 when flexible diaphragm 14 moves into outlet fluid reservoir 64 a predetermined distance.

4 Claims, 3 Drawing Sheets

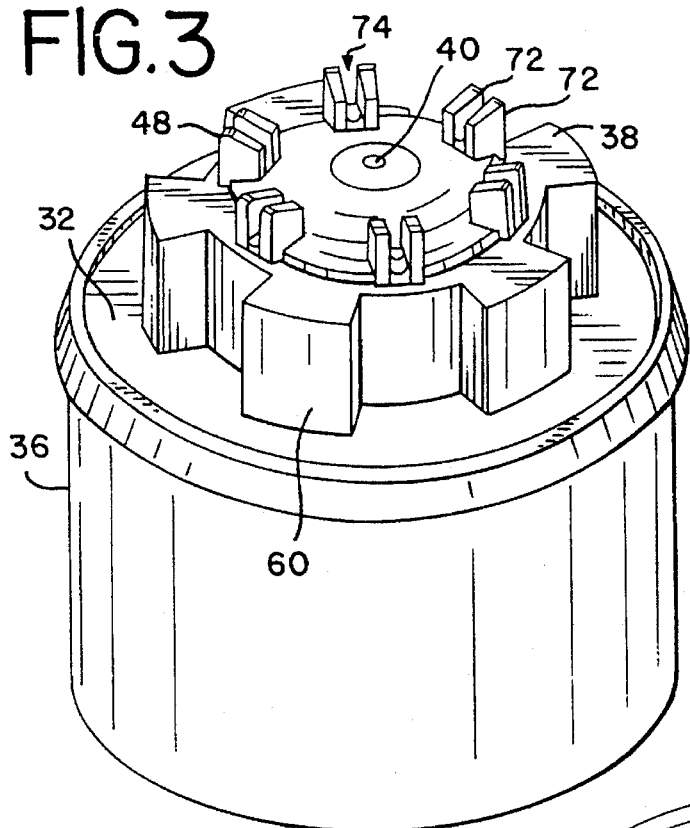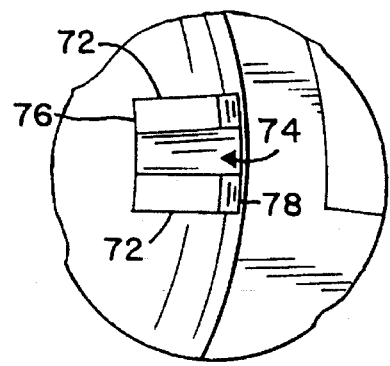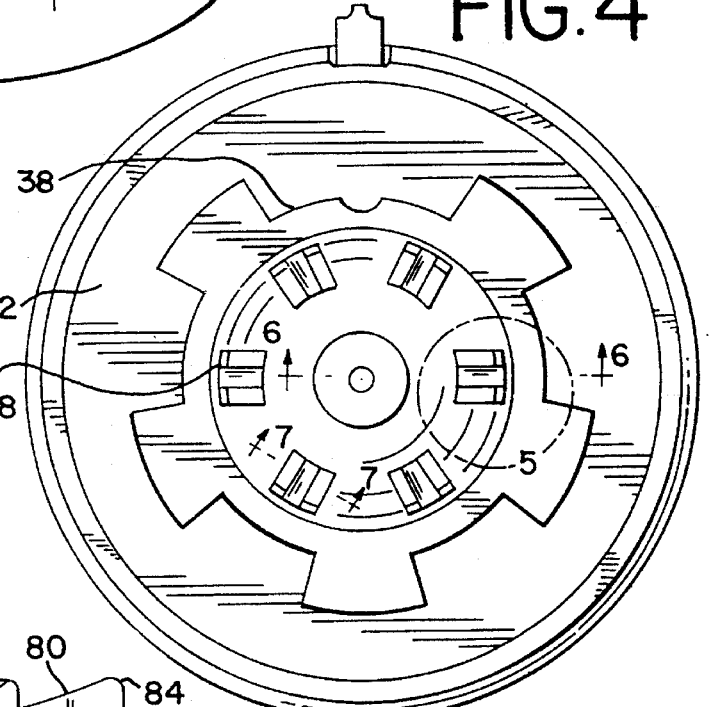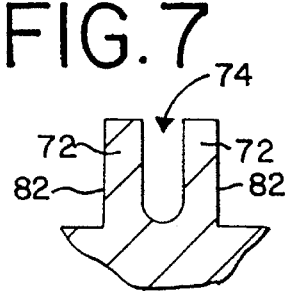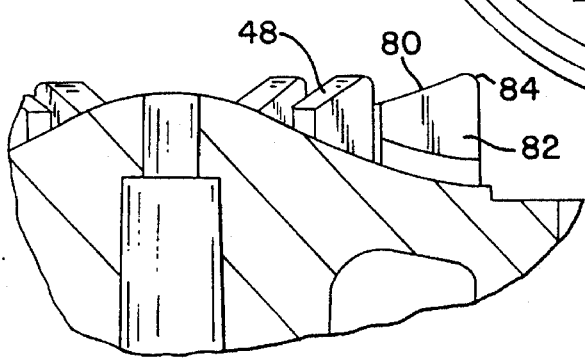

FLUID FLOW REGULATOR

FIELD OF THE INVENTION

This invention is generally directed to a flow regulator for regulating the flow of fluids. More specifically, in the medical field, this invention is directed to an intravenous fluid flow regulator for regulating the flow of intravenous fluids to a patient.

BACKGROUND OF THE INVENTION

In the medical field, medical fluids or solutions are commonly administered to patients by intravenous (I.V.) techniques. The medical fluid is usually contained within an I.V. bag which is suspended above the patient by an I.V. pole. An I.V. tubing line connects the I.V. bag of medical fluid to the patient through an I.V. needle or catheter inserted into the patient's venous system. The medical fluid flows from the elevated I.V. bag into the patient due to the force of gravity. Medical fluids can also be administered to a patient by an I.V. infusion pump connected to an I.V. tubing line. Devices that utilize these types of I.V. administration techniques are termed I.V. administration sets.

Frequently, the rate in which the medical fluid is administered to the patient must be controlled to provide proper medical treatment. Accordingly, the medical fluid is administered to the patient over an extended period of time rather than being entirely infused into the patient immediately. Of course, various medical treatments and various medical fluids may require different rates of I.V. fluid administration. The rate of I.V. fluid administration is dependant, in part, on the fluid pressure in the I.V. administration set.

Various devices and techniques have been utilized to control fluid pressure in the I.V. administration set and the corresponding fluid flow rate of the medical fluid to the patient. A clamp, for example, may be placed on the I.V. tubing line to partially restrict the flow of fluid through the tubing. However, the clamping force applied by the clamp, the amount of tubing restriction, and the control of the fluid flow rate are subject to considerable variability. Another device which purports to control the rate of fluid flow is disclosed in U.S. Pat. No. 4,343,305 to Bron, titled ADJUSTABLE-RATE, CONSTANT OUTPUT INFUSION SET (the "Bron device").

The Bron device includes a connector piece, an inlet port, a control port, an annular member, and an elastic diaphragm. The annular member is made of a rigid, substantially non-deformable material and has a step-like recess. The annular member is mounted inside the connector piece such that the diaphragm is seated in the recess. The connector piece and the diaphragm form a first chamber in communication with a fluid container via the inlet port. The connector piece and the diaphragm further form a second chamber in communication with the control port. A fluid passageway, having a flow restriction, is provided from the first chamber to the second chamber. The diaphragm is movable between positions that are close to the control port, which reduce fluid flow, and positions that are further away from the control port, which increase fluid flow. Although the Bron device purports to control the rate of fluid flow, the Bron device exhibits problems in achieving that objective. Under certain conditions, the Bron device may not control the rate of fluid flow and instead allow the fluid to flow freely or substantially unrestricted through the device. The free flow state may occur when the diaphragm slips off or tucks under the step-like recess on the annular member. The diaphragm may slip off or tuck under at a localized area or over a substantial portion of the diaphragm. When the diaphragm slips off of or tucks under the recess, a relatively large, unrestricted free flow path may be created between the first chamber and the second chamber. The fluid will flow through the unrestricted free flow path instead of the restricted passageway. Accordingly, when the diaphragm slips off of or tucks under the recess, fluid may freely flow from the fluid container to the inlet port, to the first chamber, through the free flow path to the second chamber, to the control port and then, into the patient. Compounding the problem, after the diaphragm has slipped off of or tucked under the recess the diaphragm does not return to a proper seated position on the recess. Therefore, fluid may be infused into a patient at a free flow rate instead of a controlled, reduced rate.

In use of the Bron device, it has been found that a bolus injection of fluid by a syringe into the infusion set upstream of the device may cause the diaphragm to slip off of or tuck under the annular member recess. Although medical personnel had been advised to administer bolus injections only downstream of the device, sometimes forceful, repeated upstream bolus injections occurred. It has also been found that excessive fluid container pressure may cause the diaphragm to slip off of or tuck under the annular member recess.

Therefore, a need exists to improve intravenous fluid flow regulators. Particularly, a need exists to improve intravenous fluid flow regulators by preventing fluid free flow conditions. The present invention satisfies this need. The present invention improves fluid flow regulators by providing regulators that prevent a diaphragm from slipping off of or tucking under a diaphragm holder.

Accordingly, one advantage of the present invention is to improve intravenous fluid flow regulators.

Another advantage of the present invention is to prevent fluid free flow conditions through the flow regulator.

Another advantage of the present invention is to provide a flow regulator that is resistant to misuse such as administration of bolus injections upstream of the flow regulator.

Another advantage of the present invention is to prevent a flexible diaphragm from slipping off of or tucking under a diaphragm holder.

Additional advantages of the present invention will be apparent from reviewing this specification, the drawings, and the claims.

SUMMARY OF THE INVENTION

The present invention provides an intravenous fluid flow regulator for controlling the I.V. administration of medical fluid to a patient. The fluid flow regulator provides a housing having a top and a bottom. A flexible diaphragm is positioned within the housing. A diaphragm holder is provided inside the housing for holding a sealing edge of the flexible diaphragm in fluid sealing engagement with the diaphragm holder. The housing and the flexible diaphragm define an inlet fluid reservoir and an outlet fluid reservoir. The diaphragm holder defines a by-pass fluid channel from the inlet fluid reservoir, around the diaphragm, to the outlet fluid reservoir. The flexible diaphragm being flexible to alternatively move into the inlet fluid reservoir and the outlet fluid reservoir depending on a fluid pressure differential between the inlet fluid reservoir and the outlet fluid reservoir.

A fluid inlet is connected to the housing top to provide an inlet fluid passage from an I.V. bag containing medical fluid to the inlet fluid reservoir. A fluid outlet is connected to the housing bottom to provide an outlet fluid passage from the outlet fluid reservoir to the patient.

At least one rib connected to the bottom is provided to prevent movement of the flexible diaphragm into the outlet fluid reservoir when the flexible diaphragm moves into the outlet fluid reservoir a predetermined distance.

BRIEF DESCRIPTION OF THE DRAWINGS

FIG. 3 is a perspective view of the bottom of the fluid flow regulator of FIG. 1 and FIG. 2.

FIG. 4 is a top view of FIG. 3.

FIG. 5 is an enlarged top view of a portion of FIG. 4 showing a rib in greater detail.

FIG. 6 is an enlarged side elevational view of a portion of FIG. 4 taken along line 6—6 showing the ribs in greater detail.

FIG. 7 is a cross-sectional view of a rib taken along line 7—7 of FIG. 4.

DETAILED DESCRIPTION OF PREFERRED EMBODIMENTS

Although the present invention can be made in many different forms, the preferred embodiments are described in this disclosure and shown in the attached drawings. This disclosure exemplifies the principles of the present invention and does not limit the broad aspects of the invention only to the illustrated embodiments.

Figure 1:
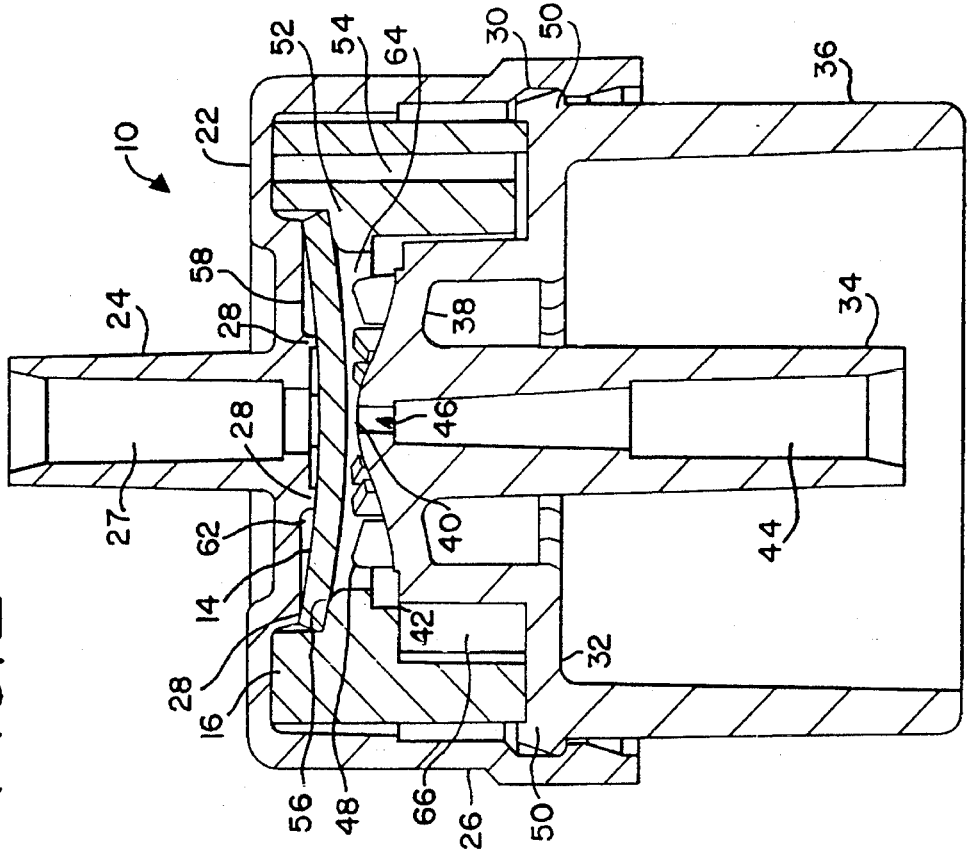
FIG. 1 is an elevational, partial cross-sectional view showing a fluid flow regulator in accordance with the present invention.
Figure 2:
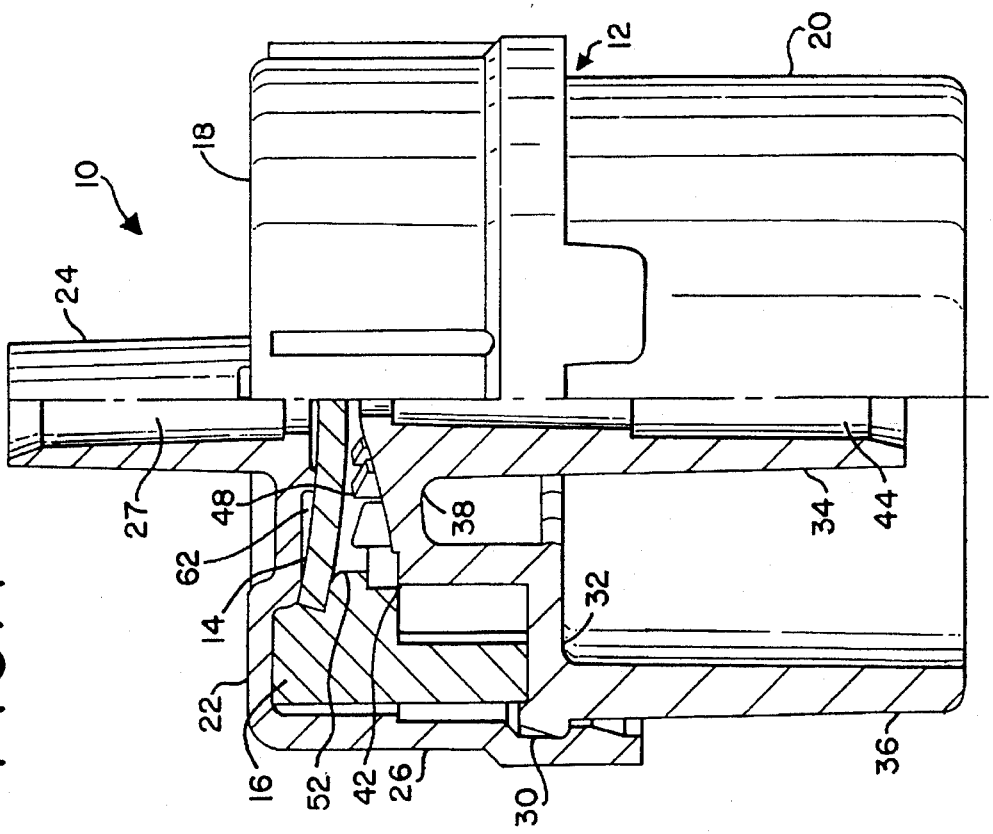
FIG. 2 is an elevational, full cross-sectional view of the fluid flow regulator of FIG. 1.

FIG. 1 shows an elevational, partial cross-sectional view of a fluid flow regulator 10 made in accordance with the present invention. FIG. 2 is a full cross-sectional view of fluid flow regulator 10 of FIG. 1 showing flow regulator 10 in greater detail. The fluid flow regulator 10 comprises a housing 12, a flexible diaphragm 14, and a diaphragm holder 16. The diaphragm 14 and diaphragm holder 16 are positioned within housing 12 as described in greater detail below.

The housing 12 comprises a top 18 and a bottom. 20. The top 18 comprises a top wall 22, a fluid inlet 24, and a top side wall 26. The top wall 22 is approximately circular in shape. The fluid inlet 24 is connected to and extends upwardly from top wall 22 and provides an inlet fluid passage 27 through top wall 22. The fluid inlet 24 is connected to top wall 22 at the center of top wall 22. A protrusion 28 is provided on top wall 22 inside top 18. The protrusion 28 contacts diaphragm 14 to bias diaphragm 14 towards bottom 20. The top wall 22 defines an arcuate capillary groove 29 that is shown more clearly in FIG. 8. The arcuate capillary groove 29 extends around the center of top wall 22 through an arc of less than 360 degrees. Preferably, capillary groove extends through an arc of 270 degrees. The function of capillary groove 29 is to provide a fluid flow restriction that causes a fluid pressure drop as fluid flows through capillary groove 29. The top wall 22 further defines a top fluid channel 31 that extends from the center of top wall 22 to capillary groove 29. As shown in FIG. 2, the top side wall 26 extends downwardly from top wall 22 around the periphery of top wall 22 and in an opposite direction from fluid inlet 24. The top side wall 26 provides a locking recess 30 for engaging bottom 20 when top 18 and bottom 20 are connected together.

The bottom 20 comprises a bottom wall 32, a fluid outlet 34, and a bottom side wall 36. The bottom wall 32 is approximately circular in shape and has a raised portion 38. The raised portion 38 has a center 40 and an edge 42. The raised portion 38 extends upwardly from bottom wall 32. The center 40 extends further from bottom wall 32 than does edge 42. The raised portion 38 slopes downwardly from center 40 to edge 42. The fluid outlet 34 is connected to raised portion 38 at center 40 and extends downwardly in an opposite direction from raised portion 38. The fluid outlet 34 provides an outlet fluid passage 44 through bottom wall 32 via an outlet opening 46 in raised portion 38. A plurality of ribs 48, discussed in detail below, are provided on raised portion 38. The bottom side wall 36 extends downwardly from bottom wall 32 around the periphery of bottom wall 32 and in the same direction as fluid outlet 34. The bottom side wall 36 provides a locking ridge 50 for engaging top 18, particularly locking recess 30, when top 18 and bottom 20 are connected together.

The diaphragm holder 16 has an annular ring shape and an annular ledge 52. The annular ledge 52 extends from diaphragm holder 16 towards the inside of the annular ring shape of diaphragm holder 16. The annular ledge 52 sealingly engages diaphragm 14. The diaphragm holder 16 provides a by-pass fluid channel 54 through at least a portion of diaphragm holder 16. The by-pass fluid channel 54 permits fluid to flow around diaphragm 14 as described below. The diaphragm holder 16 is constructed of a flexible, resilient material.

The diaphragm 14 is generally circular in shape and is constructed from a flexible, resilient material. The diaphragm 16 has a fluid sealing edge 56 and a middle 58. The sealing edge 56 contacts annular ledge 52 of diaphragm holder 16. The middle 58 contacts protrusion 28 of top wall 22 of top 18. The contact between sealing edge 56 and annular ledge 52 is a fluid tight seal.

The fluid flow regulator 10 is assembled as shown in FIG. 2. The top 18 and bottom 20 are connected together to form housing 12. The top 18 and bottom 20 are concentrically aligned such that fluid inlet 24 and fluid outlet 34 are concentrically aligned. The locking ridge 50 on bottom 20 engages locking recess 30 on top 18 to lockingly connect top 18 and bottom 20 together. The top 18 and bottom 20 are locked together to prevent movement along a central axis. Although, top 18 and bottom 20 can be rotated relative to each other around the central axis. The flexible, resilient diaphragm holder 16 is positioned within housing 12 and between top 18 and bottom 20. The diaphragm holder 16 is concentrically aligned with top 18 and bottom 20. When top 18 is rotated relative to bottom 20, diaphragm holder 16 also rotates relative to top 18 but does not rotate relative to bottom 20. The bottom 20 is provided with tabs 60, shown more clearly in FIG. 3, that engage tab recesses in diaphragm 14 to prevent diaphragm 14 from rotating relative to bottom 20.

When top 18 and bottom 20 are connected together, diaphragm holder 16 is compressed between top 18 and bottom 20. The compression of resilient diaphragm holder 16 imparts a decompression force on top 18 and bottom 20 that tends to separate top 18 and bottom 20. However, top 18 and bottom 20 do not automatically separate because top 18 and bottom 20 are locked together by locking recess 30 and locking ridge 50. The top 18 and bottom 20 can be separated by spreading top side wall 26 outwardly from locking ridge 50 to allow locking ridge 50 to disengage from locking recess 30.

The flexible, resilient diaphragm 14 is positioned within housing 12 and between top 18 and bottom 20 to form an inlet fluid reservoir 62 and an outlet fluid reservoir 64. The diaphragm 14 is concentrically aligned with top 18, diaphragm holder 16, and bottom 20. When top 18 and bottom 20 are locked together protrusion 28 contacts middle 58 of diaphragm 14 and biases diaphragm 14 towards outlet fluid reservoir 64. Biasing diaphragm 14 towards outlet fluid reservoir 64 causes sealing edge 56 of diaphragm 14 to press against annular ledge 52, in sealing engagement. In this manner, diaphragm holder 16 holds diaphragm 14 within housing 12. While sealing edge 56 is held in sealing engagement against annular ledge 52, middle 58 of diaphragm 14 remains flexible to alternatively move towards fluid outlet 34 and fluid inlet 24 as described below in operation of flow regulator 10. Briefly, as middle 58 of diaphragm 14 moves towards fluid outlet 34, middle 58 forms an arcuate shape. The arcuate shape has a radius of curvature that increases as middle 58 moves closer to fluid outlet 34.

Figure 8:
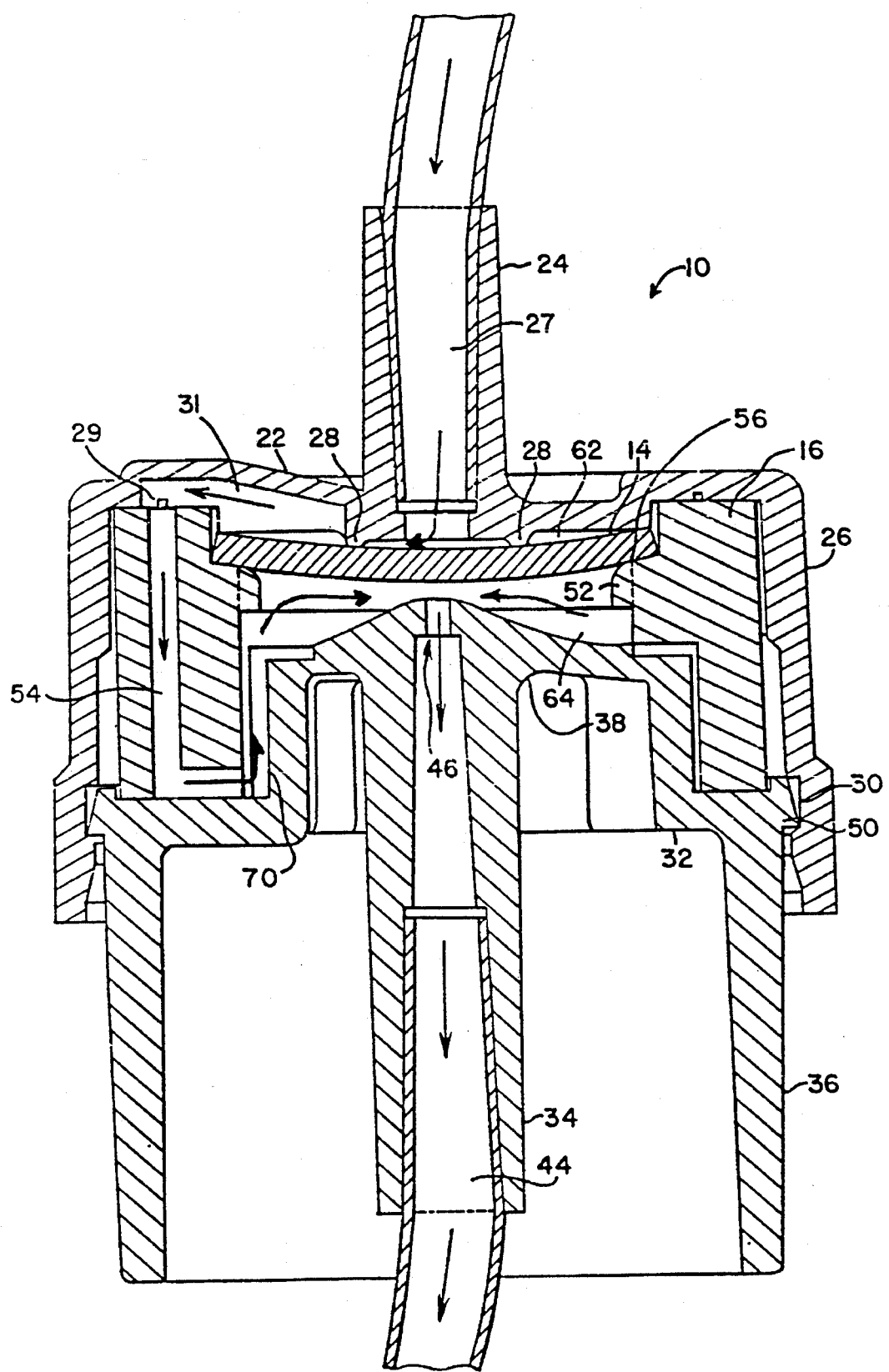
FIG. 8 is a cross-sectional view of the fluid flow regulator showing the fluid flow path through the regulator.

A fluid flow path through fluid flow regulator 10 will now be described while referring to FIG. 8. The fluid enters fluid flow regulator 10 through inlet fluid passage 27 in fluid inlet 24. The fluid flows from inlet fluid passage 27 into inlet fluid reservoir 62. The fluid flows from inlet fluid reservoir 62 through top fluid channel 31 in top 18 to capillary groove 29 in top 18. The fluid flows from capillary groove 29 to by-pass fluid channel 54 in diaphragm holder 16. The fluid flows from by-pass channel 54 through a bottom fluid channel 70 between diaphragm holder 16 and bottom 20. The fluid flows from bottom fluid channel 70 to outlet fluid reservoir 64. Then, the fluid flows from outlet fluid reservoir 64 through outlet fluid passage 44 in fluid outlet 34.

The flow channels 31, 54, 70 are sufficiently large enough to allow fluids to flow through channels 31, 54, 70 relatively unrestricted. However, capillary groove 29 is sufficiently small enough to restrict fluid flow through capillary groove 29. Preferably, the size of capillary groove 29 varies from a relatively large groove, having a large width and depth, to a relatively small groove, having a small width and depth. As fluid flows through capillary groove 29 a fluid pressure drop occurs because capillary groove 29 restricts fluid flow. The amount of pressure drop or decrease and thus, the flow rate through regulator 10, can be controlled by varying the effective length of capillary groove 29.

The effective length of capillary groove 29 is the length of capillary groove 29 that fluid must flow through to enter by-pass fluid channel 54. The effective length of capillary groove 29 can be equal to or less than the entire length of capillary groove 29. The effective length of capillary groove 29 can be varied by rotating top 18 in relation to diaphragm holder 16 and bottom 20. When top 18 rotates relative to diaphragm holder 16, capillary groove 29 rotates to connect by-pass fluid channel 54 to capillary groove 29. The fluid flows through the effective length of capillary groove 29 to enter by-pass fluid channel 54 at the connection location. Therefore, the connection location along the length of capillary groove 29 determines the effective length of capillary groove 29, the resulting fluid pressure drop, and the resulting fluid flow rate through regulator 10.

FIG. 3 shows a perspective view of bottom 20 of fluid flow regulator 10 including ribs 48. The ribs 48 are provided on raised portion 38 of bottom wall 32 to prevent diaphragm 14 from slipping off of or tucking under annular ledge 52 of diaphragm holder 16 when diaphragm 14 moves into outlet fluid reservoir 64. The ribs 48 are connected to and extend upwardly from raised portion 38. The ribs 48 extend into outlet fluid reservoir 64 towards diaphragm 14. FIG. 3 shows six ribs 48 on raised portion 38; although, the number of ribs 48 can be increased or decreased. Preferably, there are a sufficient number of ribs 48 to prevent diaphragm 14 from slipping off of or tucking under any portion of annular ledge 52. Each rib 48 comprises two upstanding rib columns 72 spaced apart by a column space 74. One alternative rib 48 configuration would include a single rib column 72 rather than two rib columns 72 spaced apart by column space 74.

FIG. 4 shows a top view of bottom 20 of fluid flow regulator 10 from FIG. 3. The ribs 48 are symmetrically positioned on raised portion 38 surrounding outlet opening 46. Particularly, ribs 48 are located at a constant radial distance from the center of outlet opening 46. The radial distance from the center of outlet opening 46 is short enough so that ribs 48 do not interfere with diaphragm holder 16 when flow regulator 10 is assembled. Ribs 48 do not touch diaphragm holder 16 and thus, do not interfere with the compression of diaphragm holder 16. The ribs 48 are also spaced at equal arcuate angles around the center of outlet opening 46. However, the ribs 48 may be positioned asymmetrically, including various radial distances and various arcuate angles, on raised portion 38.

FIG. 5 shows an enlarged top view of a portion of bottom 20 with rib 48 shown in greater detail. The two upstanding rib columns 72 of rib 48 are spaced apart by column space 74. A rib 48 constructed of two, relatively thin rib columns 72 is preferred over a single, relatively wider rib column 72. The two rib column 72 structure provides fluid flow through column space 74. The rib 48 has a rib front 76 facing outlet opening 46 and a rib back 78 facing away from outlet opening 46. The rib front 76 and rib back 78 have arcuate profile shapes as shown in FIG. 5. The arcuate profile shapes have a radial center located at the center of outlet opening 46.

FIG. 6 shows an enlarged side view of rib 48 taken along line 6—6 from FIG. 4. FIG. 6 further shows a portion of bottom 20 in cross-section. Each rib 48 has a rib top 80 and a pair of rib sides 82. The rib top 80 connects rib front 76, rib back 78, and rib sides 82 together. The junction of rib top 80 with rib back 78 is a rounded corner 84. The rounded corner 84 extends into outlet fluid reservoir 64 further than does raised portion 38 at outlet opening 46. The junction of rib top 80 with rib front 76 extends into outlet fluid reservoir 64 a lesser distance than does the junction of rib top 80 with rib back 78. Thus, the rib top 80 slopes downwardly from rib back 78 towards rib front 76. The profile shape of sloping rib top 80 as shown in FIG. 6 is curved or arcuate. The arcuate shape of rib top 80 is spaced (preferably 0.02 inches) from diaphragm 14 when diaphragm 14 extends into outlet fluid reservoir 64 far enough to contact and close off outlet opening 46. The rib 48 extends into outlet fluid reservoir 64 a predetermined distance so that rib 48 does not contact diaphragm 14 under normal operating conditions as described below. Likewise, the diaphragm 14 contacts rib 48 when diaphragm 14 moves into outlet fluid reservoir 64 a predetermined distance.

FIG. 7 shows a cross-sectional view of rib 48 taken along line 7—7 of FIG. 4. Particularly, FIG. 7 shows the profile shape of column space 74 between rib columns 72. The profile of column space 74 has a semicircular shape at the bottom where rib 48 is attached to raised portion 38 of bottom wall 32 of bottom 20.

In operation of fluid flow regulator 10, regulator 10 is connected to an I.V. administration set. The I.V. administration set includes an I.V. bag containing medical fluid. The I.V. bag is connected to fluid inlet 24 by I.V. tubing. The fluid outlet 34 is connected to another piece of I.V. tubing which is connected to an I.V. needle. The needle is inserted into a patient's venous system. The I.V. set may include other I.V. components, for example, a drip chamber or a Y-type injection site.

The fluid flow regulator 10 is adjusted to set the desired fluid flow rate by rotating top 18 in relation to diaphragm holder 16 and bottom 20. The medical fluid flows under the force of gravity from the I.V. bag to fluid flow regulator 10. The fluid enters fluid flow regulator 10 through inlet fluid passage 27 in fluid inlet 24. The fluid flows through inlet fluid passage 27 to inlet fluid reservoir 62. The fluid contained in inlet fluid reservoir 62 has an inlet fluid pressure. The fluid flows around diaphragm 14 by flowing through by-pass fluid channel 54 in diaphragm holder 16. More specifically, the fluid flows around diaphragm 14 by flowing through top fluid channel 31, by-pass fluid channel 54, and bottom fluid channel 70. The fluid flows into outlet fluid reservoir 64 from bottom fluid channel 70. The fluid contained in outlet fluid reservoir 64 has an outlet fluid pressure. The fluid flows from outlet fluid reservoir 64 through outlet fluid passage 44 in fluid outlet 34. The fluid then flows from fluid outlet 34 through the I.V. tubing into the patient.

As the fluid flows from inlet fluid reservoir 62 through capillary groove 29 to outlet fluid reservoir 64, a fluid pressure drop occurs. Commonly known fluid dynamics analysis techniques can be utilized to determine the amount of pressure drop. Accordingly, a pressure differential is created between inlet fluid reservoir 62 and outlet fluid reservoir 64. The outlet fluid pressure in outlet fluid reservoir 64 is less than the inlet fluid pressure in inlet fluid reservoir 62. The pressure differential causes flexible diaphragm 14 to flex or move into outlet fluid reservoir 64. Particularly, the middle 58 of diaphragm 14 moves into outlet fluid reservoir 64.

As diaphragm 14 moves into outlet fluid reservoir 64 diaphragm 14 moves closer to outlet opening 46 of outlet fluid passage 44. Fluid flow through outlet opening 46 is restricted and reduced as diaphragm 14 approaches outlet opening 46. The diaphragm 14 may contact bottom 20 at outlet opening 46 to close off outlet opening 46. Fluid flow through flow regulator 10, and particularly through capillary groove 29 is reduced in relation to the reduction of fluid flow through outlet opening 46. Because the fluid flow rate through capillary groove 29 is reduced, the pressure drop through capillary groove 29 is also reduced. Accordingly, the pressure differential between inlet fluid reservoir 62 and outlet fluid reservoir 64 is reduced. The resilient, flexible diaphragm 14 moves away from outlet opening 46 and back towards inlet fluid reservoir 62 due to the reduced fluid pressure differential.

The fluid flow rate through flow regulator 10 will increase as diaphragm 14 moves away from outlet opening 46 because flow through outlet opening 46 is less restricted by diaphragm 14. The pressure differential and corresponding fluid flow rate will change repetitively as described above until an equilibrium flow rate is established. The equilibrium flow rate is established relatively quickly such that the process of establishing equilibrium fluid flow does not adversely effect administration of the fluid to the patient.

The inlet fluid pressure may change due to various circumstances. For example, the inlet fluid pressure will decrease over time as the amount of fluid in the I.V. bag decreases. Also, the height of the I.V. bag above the patient may be changed. These fluid pressure changes can be measured by the amount of head height above the regulator. As the fluid inlet pressure changes, fluid flow regulator 10 compensates for the pressure change by establishing an equilibrium as described above. A fluid flow regulator 10 constructed in accordance with the present invention has been found to maintain average fluid flow rates within plus or minus ten percent variation despite head height movement between 30 and 60 inches. In this manner, fluid flow regulator 10 maintains a constant fluid flow rate through the device.

The fluid flow regulator 10 may be misused by injecting a bolus injection of supplementary fluid medication in the I.V. set upstream of regulator 10. The bolus injection of fluid may cause an extreme pressure increase in the inlet fluid reservoir. The extreme pressure increase can be compounded by repeated, forceful upstream bolus injections. The pressure increase will cause the flexible diaphragm 14 to move into outlet fluid reservoir 64, and under normal use regulator 10 would compensate for the increased pressure. However, the extreme pressure increase may move pressure sensitive diaphragm 14 far into outlet fluid reservoir 64 and, if not for ribs 48, cause diaphragm 16 to slip off of or tuck under annular ledge 52. Under the extreme pressure, diaphragm 14 moves into contact with ribs 48 which prevent further movement of diaphragm 14 into outlet fluid reservoir 64. The ribs 48 are positioned on bottom 20 and extend into outlet fluid reservoir 64 such that diaphragm 14 abuts ribs 48 when diaphragm 14 moves into outlet fluid reservoir 64 a predetermined distance. The predetermined distance or maximum movement of diaphragm 14 is small enough to prevent diaphragm 14 from slipping off of or tucking under annular ledge 52.

While the preferred embodiments have been illustrated and described, numerous changes and modifications can be made without significantly departing from the spirit and scope of this invention. Therefore, the inventors intend that such changes and modifications be covered by the appended claims.

What is claimed is:

1. A device for regulating the flow of intravenous fluid comprising;

a housing including a top defining an inlet fluid passage, a bottom defining an outlet fluid passage, the top being rotatably connected to the bottom;

a generally disk like diaphragm within the housing, the diaphragm defining an inlet reservoir in fluid communication with the inlet passage and an outlet reservoir in fluid communication with the outlet passage, the bottom forming an outlet opening between the outlet reservoir and the outlet passage, the diaphragm including an outer circumferential sealing edge;

means within the housing for sealingly clamping the sealing edge, the diaphragm being constructed to flex into the outlet and inlet reservoirs and closingly engage the outlet opening;

a passageway formed within the housing and having an effective length from the inlet reservoir to the outlet reservoir, the housing including means for varying the effective length upon rotation of the top relative to the bottom; and a plurality of ribs disposed about the outlet opening, the ribs being constructed to engage the diaphragm while the diaphragm closingly engages the outlet opening and prevent the sealing edge from disengaging from the clamping means upon the introduction of the fluid under excessively high pressure into the inlet reservoir.

2. The device of claim 1 wherein the clamping means includes a diaphragm holder, the diaphragm holder forming a portion of the passageway.

3. The device of claim 1 wherein the top forms a restricting groove of varying size, the groove forming a portion of the passageway.

4. The device of claim 1 wherein the ribs are configured to engage the diaphragm only after the outlet opening is closingly engaged.

* * * * *